United States Patent [19]

Weinberg et al.

[11] Patent Number: 4,604,166
[45] Date of Patent: Aug. 5, 1986

[54] APPARATUS AND PROCESS FOR REDUCING PERISTALTIC PUMP NOISE IN A HIGH IMPEDANCE ELECTROCHEMICAL MEASURING SYSTEM

[75] Inventors: Melvin S. Weinberg, Nashua, N.H.; Alan D. Cormier, Newburyport, Mass.; Ronald L. Jones, Newton, N.H.

[73] Assignee: Amdev, Inc., Haverhill, Mass.

[21] Appl. No.: 645,018

[22] Filed: Aug. 28, 1984

[51] Int. Cl.[4] ............................................. G01N 27/46
[52] U.S. Cl. .................................... 204/1 T; 204/400; 204/416; 422/82; 73/864.34
[58] Field of Search ................ 204/1 T, 400, 416–420; 422/82; 73/864.34; 417/477

[56] References Cited

U.S. PATENT DOCUMENTS

| | | | |
|---|---|---|---|
| 2,563,062 | 8/1951 | Perley | 204/420 |
| 3,471,262 | 10/1969 | Hrdina | 422/82 |
| 3,840,438 | 10/1974 | Ast et al. | 204/420 |
| 4,218,197 | 8/1980 | Meyer et al. | 417/477 |
| 4,360,415 | 11/1982 | Brezinski | 204/435 |
| 4,399,362 | 8/1983 | Cormier et al. | 422/82 |

*Primary Examiner*—T. Tung
*Attorney, Agent, or Firm*—Wolf, Greenfield & Sacks

[57] ABSTRACT

Apparatus and a process for reducing peristaltic pump noise in a high impedance electrochemical measuring system by eliminating the noise at the pump source so as to minimize the effect of the noise on the precision and the response time of the measuring electrode. In a system having a high impedance measuring electrode connected to the elastomeric peristaltic tubing via a fluid conduit, a high impedance segment is disposed in the fluid conduit between the electrode and peristaltic tubing and means are disposed between the segment and peristaltic tubing for discharging the electrical noise generated by the action of the pump rollers over the peristaltic tubing. Preferably the discharging means is a conductive path electrically connected to an AC capacitive ground wherein the impedance of the capacitive ground is less than that of the segment. The segment may be a nonconductive liquid or gas such as air.

18 Claims, 4 Drawing Figures

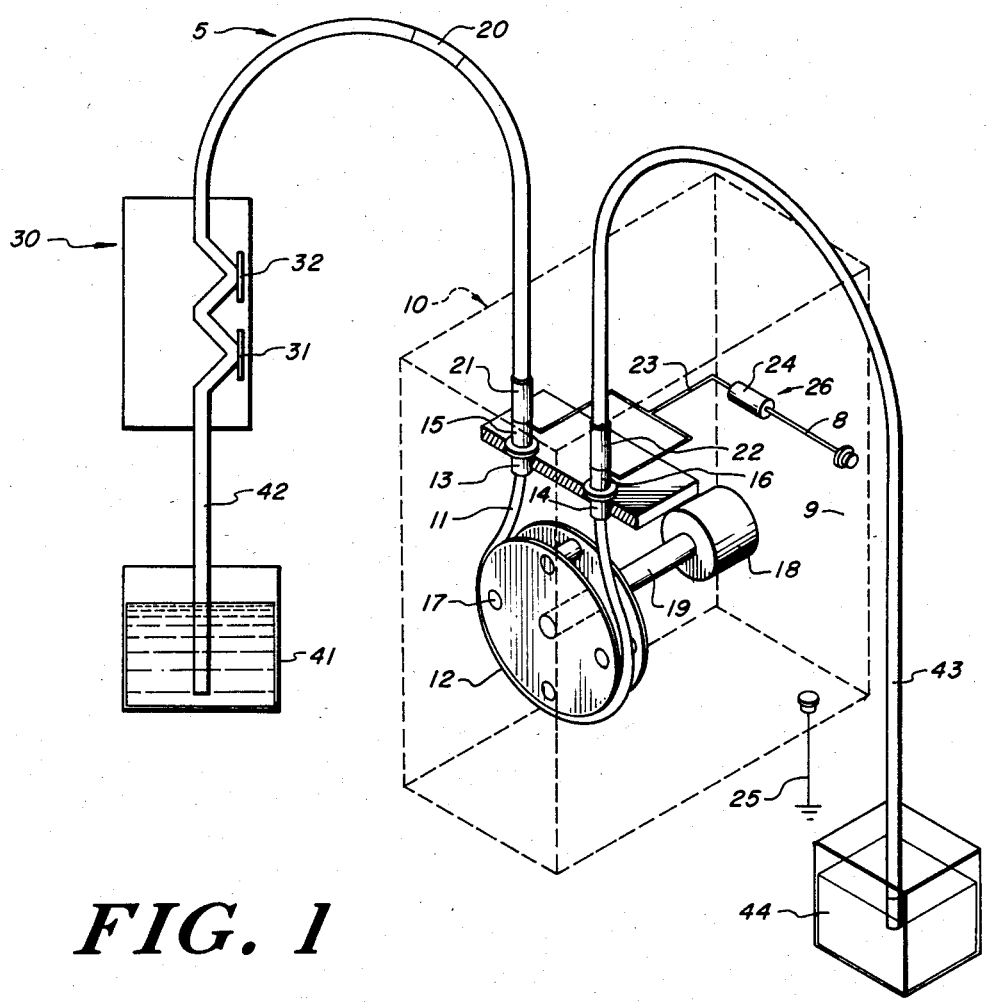
FIG. 1
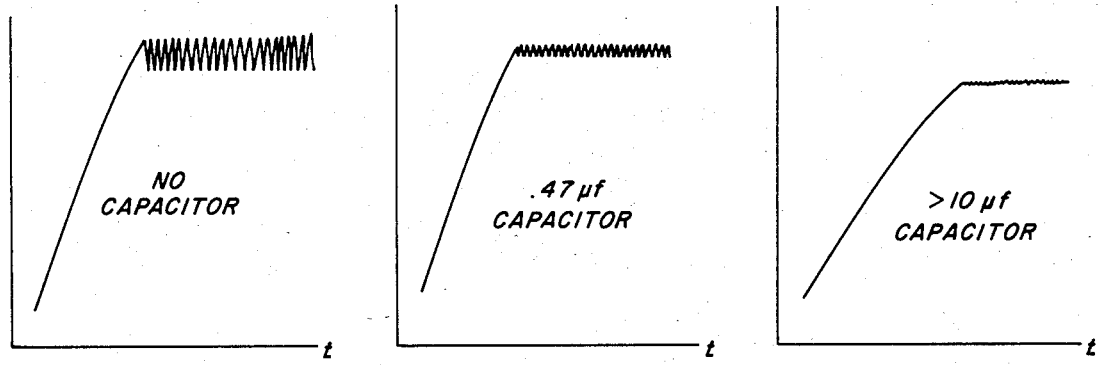
FIG. 2A  FIG. 2B  FIG. 2C

APPARATUS AND PROCESS FOR REDUCING PERISTALTIC PUMP NOISE IN A HIGH IMPEDANCE ELECTROCHEMICAL MEASURING SYSTEM

FIELD OF THE INVENTION

This invention relates to apparatus and a process for reducing peristaltic pump noise in a high impedance electrochemical measuring system.

BACKGROUND OF THE INVENTION

Electrochemical measuring apparatus for determining the pH or the gas or ion concentration of biological fluids such as blood typically include a high impedance electrode device as the sensor. For example, to measure pH, sodium, potassium, or chloride, high impedance measuring electrodes in the range of 100 to 3,000 megaohms are used. These high impedance electrodes can be effected by externally generated voltages from sources such as RF antennas and from other sources of electromagnetic, static electric, and galvanic activity.

A peristaltic pump is typically used in electrochemical measuring systems to move the sample fluid past the measuring electrodes. A simple peristaltic pump consists of one or more rollers in contact with an elastomeric tubing through which the fluid flows. The peristaltic tubing is generally stretched over the rollers to pinch (close off) the tubing at one or more points of contact. Fluid entrapped by the contact points is pushed through the tubing by the action of the rollers moving along the stretched tubing.

Common elastomeric materials used in peristaltic pumps (e.g., silicone and soft PVC) can generate a static charge when a pump roller contacts and rolls and/or slides over the surface to move the fluid within the tube. Such build-up is conducted through the pumped fluid and can be detected in the high impedance measuring devices as "amplified peristaltic noise". The frequency of noise is dependent on the pump cycle and the number of rollers in the pump. The net effect is a degradation of the precision of the analytical measurements.

Previous attempts to eliminate peristaltic noise have involved electronic filtering between the measuring electrode and meter by either an analogue filter or by digital methods. Such filtering is undesirable because it dampens the entire signal coming from the electrode, both the ion measuring component and noise. Further, analogue capacitive filtering at the measuring electrodes is undesirable because the capacitance effects an increase in the response time of the electrode. Digital filtering is expensive and requires additional time to make computations.

SUMMARY OF THE INVENTION

It is an object of this invention to provide an apparatus and process for reducing peristaltic noise in a high impedance electrochemical measuring system without significantly effecting the precision or the response time of the measuring electrode.

Another object of this invention is to provide an inexpensive, rapid, and automatic means for reducing peristaltic noise in a high impedance measuring system.

Still another object of this invention is to provide a means for reducing peristaltic pump noise at the noise source so as to minimize the effect on the measuring electrode.

According to the invention, apparatus is provided for reducing peristaltic noise in a high impedance electrochemical measuring system which includes a peristaltic pump having an elastomeric peristaltic tubing and roller means for compressing the tubing to cause a pumping action on fluid therein, and a high impedance measuring electrode connected to the peristaltic tubing via a fluid conduit. A high impedance segment is disposed in the fluid conduit between the electrode and peristaltic tubing and means are disposed between the segment and peristaltic tubing for discharging the electrical noise generated by the action of the pump rollers over the peristaltic tubing. Preferably the discharging means is a conductive path electrically connected to an AC capacitive ground, the AC capacitive ground having an impedance less than the segment. The conductive path is preferably a tubular member in fluid connection with the peristaltic tubing or a probe inserted adjacent the inlet end of the tubing. Further, a second conductive path may be disposed adjacent the outlet end of the peristaltic tubing.

The high impedance segment is preferably a nonconductive gas or liquid selected from the group consisting of air, nitrogen, carbon dioxide, argon, flurocarbon liquids and liquid silicone. Preferably the impedance of the segment is more than double the impedance of the AC capacitive ground.

In a preferred embodiment the electrode has an impedance of from about 100 to about 3,000 megaohms, more preferably from about 500 to about 1,500 megaohms, and the capacitor has a capacitance of from about 0.1 to about 10 microfarads ($\mu f$), more preferably from about 0.1 to about 1.0 $\mu f$, and most preferably from about 0.4 to about 0.6 $\mu f$.

The invention also includes a process for reducing peristaltic noise in a high impedance electrochemical measuring system which includes a peristaltic pump connected to a high impedance electrode via a fluid conduit, the process comprising the steps of introducing a high impedance segment into the fluid conduit between the electrode and peristaltic tubing and inserting means between the segment and peristaltic tubing for discharging the electrical noise generated by the action of the pump rollers over the peristaltic tubing.

BRIEF DESCRIPTION OF THE DRAWINGS

The above and other features, objects and advantages of the present invention will be better understood from a reading of the specification in conjunction with the following drawings in which:

FIG. 1 is a perspective view of the reduced noise electrochemical measuring system of this invention; and FIGS. 2A, 2B and 2C are three graphs showing the effect of capacitor size on electrode response.

DETAILED DESCRIPTION OF THE PREFERRED EMBODIMENTS

With reference to FIG. 1, a peristaltic pump 10 is connected to an electrochemical testing unit 30 by a fluid conduit 5 in order to pump a sample fluid to be analyzed past the high impedance measuring and reference electrodes 31, 32, respectively, in the testing unit. The sample fluid travels from the sample container 41 through each of the supply tube 42, the testing unit 30, the fluid conduit 5, the peristaltic tubing 11, and the waste tube 43, and into waste container 44. A continuous fluid passage is thus defined between the sample container and waste container. Typical sample fluids include blood, plasma, serum, spinal fluid, urine and intracellular fluid.

The action of a pump roller assembly 12 on the peristaltic tubing 11 causes the sample fluid to flow through the continuous fluid passage. The elastomeric peristaltic tubing 11 has inlet and outlet ends 13, 14 connected to the fluid conduit 5 and waste tube 43 respectively, at fixed end posts 15, 16. The peristaltic tubing 11 is stretched over three of the four rollers 17 of the roller assembly to pinch (close off) the tubing at three points of contact. The roller assembly is connected to a stepper motor 18 by a shaft 19 and rotation of the shaft causes the rollers to rotate and move along peristaltic tubing 11 forcing the fluid trapped between one or more contact points to move through the peristaltic tubing. The operation of the pump is conventional and an off-the-shelf peristaltic pump of known construction may be used in this invention.

When the pump rollers contact and roll and/or slide over the surface of the common elastomeric materials used in peristaltic pumps, such as silicone and soft PVC (e.g., "Tygon" sold by the U.S. Stoneware Co., Akron, Ohio), a static charge is generated. The rubbing roller on the stretched tubing strips electrons from atoms at the surface of the tubing and the tubing becomes positively charged (i.e., loses electrons) while the fluid becomes negatively charged (gains electrons). A changing electrostatic space field is created in response to the pump cycle and this charge build-up is conducted through the pumped fluid and tubing and is detected by the high impedance electrodes as "amplified peristaltic noise". Its effect is to degrade the precision of the measurements taken at the electrodes.

To minimize the effect of this static charge on the high impedance electrodes, the peristaltic pump and fluid conduit are modified in this invention to provide a high degree of electrical isolation. This is accomplished by introducing a high impedance segment 20 in the fluid conduit 5 between the high impedance electrodes 31, 32 and the peristaltic tubing 11 and further by introducing discharging means between the segment 20 and peristaltic tubing 11. Preferred discharging means are conductive paths such as electrically conductive tubular members 21, 22 disposed in fluid connection at the inlet and outlet ends of the peristalic tubing and connected via conductive wire 23 to an AC or capacitive ground 26. Tubular members 21, 22 can be any electrically conductive material such as metal or a metal particle filled or carbon filled material, such as silver impregnated silicone. If an elastomeric and electrically conductive material is used as the peristaltic tubing, the tubing itself can serve as the conductive path. Alternatively, electrically conductive probes may be inserted through the fluid conduit, peristaltic tubing, or waste tube adjacent the inlet and outlet ends of the peristaltic tubing and the probes electrically connected to the capacitive ground to achieve a similar conductive path.

The impedance of the AC capacitive ground is less than the impedance of the segment so that the static charges built up in the peristaltic tubing 11 are discharged through the capacitor 24 to ground 25. As shown in FIG. 1, the capacitor 24 is electrically connected to the wall 9 of pump 10 by a conductive wire 8 and the pump wall is grounded by grounding stud 25. A direct ground is not used in order to avoid ground loops which also effect high impedance devices.

The high impedance segment may be any nonconductive gas or liquid such as air, nitrogen, carbon dioxide, argon, fluorocarbon liquids, or silicone liquid. Preferably the segment is air. The length of the segment is preferably greater than about 0.5 inch such as from about 2 inches to about 6 inches, and may occupy the entire distance between the testing unit and pump.

The high impedance segment 20 is introduced into fluid conduit 5 through the supply tube 42. Prior to inserting supply tube 42 in sample container 41, the pump 10 is turned on and air is allowed to enter the supply tube. The supply tube is then inserted in sample container 41 to fill supply tube 42 with sample fluid and the air segment travels through supply tube 42 and testing unit 30 to fluid conduit 5 before measurements of the sample fluid are taken by the electrodes. In this manner an air segment is introduced into the fluid conduit 5 between each sample fluid.

The size of the capacitor is selected in order to reduce the peristatlic noise without at the same time substantially effecting the response time or accuracy of the high impedance electrode. Based on the amount of dampening required, the smallest capacitor that will achieve this dampening should be selected. Shown in FIG. 2 are graphs illustrating the effect of capacitor size on the electrode response. In FIG. 2A where no capacitor is used, the electrode response is fast (high slope curve) but the noise represented by the deep peaks and valleys at the top of the curve make an accurate reading difficult. In FIG. 2B where a 0.47 $\mu f$ (microfarad) capacitor is used, the response time is not significantly reduced but the noise at the top of the curve is substantially reduced to enable an accurate measurement to be made. In FIG. 2C where a greater than 10 $\mu f$ capacitor is used, the response time is substantially reduced (reduced slope of curve) and the peak of the curve, while smooth due to the reduction of noise, never attains the true value. Thus, the objective is to use the smallest capacitor which will achieve the desired amount of damping to enable an accurate reading without sufficiently reducing the response time and without suppressing the peak so that an accurate measurement can not be made.

By using the apparatus and method of this invention, dampening of the peristaltic noise of 60–70% and up to about 200% has been achieved without significant effect on the electrode response time. The apparatus is useful with electrodes ranging from about 100 to about 3,000 megaohms, and preferably from about 500 to about 1,500 megaohms. The size of the capacitor may range from about 0.1 to about 10 $\mu f$, preferably from about 0.1 to 1.0 $\mu f$, and more preferably from about 0.4 to about 0.6 $\mu f$.

In the process of the invention for reducing peristaltic pump noise in a high impedance electrochemical measuring system including a peristaltic pump connected to a high impedance electrode via a fluid conduit, the process includes introducing a high impedance segment into the fluid conduit between the electrode and peristaltic tubing and inserting means between the segment and peristaltic tubing for discharging the peristaltic noise generated by the action of the pump rollers over the peristaltic tubing.

The following example is set forth primarily for the purpose of illustration and the specific enumeration should not be construed as a limitation on the concept of this invention.

EXAMPLE

A high impedance electrochemical measuring system as shown in FIG. 1 was constructed and tested with aqueous sodium and aqueous potassium solutions for reduction in peristaltic pump noise. The electrochemical testing unit was the ISE ion selective module sold by AMDEV, Inc., Haverhill, Mass., containing a 1,500 megaohm sodium selective electrode and a 500 megaohm potassium selective electrode. The fluid conduit, supply tube, and waste tube were ethyl vinylacetate tubing (about 0.030 inch I.D., about 0.060 inch O.D.) sold by Thermal Plastic Process, Warren, N.J. The peristaltic tubing was 8 centimeters in length (unstretched) Silastic silicone tubing (0.062 inch I.D., 0.125 inch O.D.) sold by Dow Corning Corporation, Midland, Mich. The peristaltic tubing was stretched approximately 20% over a pump roller assembly having 4 rollers. Two thin wall 19 gauge hypodermic stainless steel tubular electrical connectors were positioned at the inlet and outlet ends of the peristaltic tubing. An 18 to 20 gauge tin coated copper conductive wire connected the electrical connectors to a 0.47 $\mu f$ capacitor and ground. A 3 to 4 inch air segment was introduced into the fluid conduit between the peristaltic tubing and electrode module.

An aqueous sodium solution of about 140 meq/L (milliequivalents/liter) of sodium was run through the system first with the filter (i.e., air segment and capacitive ground) disconnected and then with the filter connected. With the filter disconnected the average deviation (peak to cusp) of the electrode reading was about ±0.3 mV (±1.6 meq Na+/L). With the filter connected the average deviation was reduced to about ±0.1 mV (±0.5 meq Na+/L), an approximately 200% improvement in dampening out the peristaltic noise.

An aqueous potassium solution of about 4 meq/L of potassium was then run through the system. Without the filter connected the average devication was about ±0.3 mV (±0.05 meq K+/L) and with the filter connected the average deviation was about ±0.1 mV (±0.02 meq K+/L), an approximately 200% improvement in noise reduction.

Having described the invention in detail, those skilled in the art will appreciate that numerous modifications may be made thereof without departing from the spirit of the invention. Therefore, it is not intended that the scope of the invention be limited to the specific embodiment illustrated and described. Rather, it is intended that the scope of the invention be determined by the appended claims and their equivalents.

What is claimed is:

1. An improved high impedance electrochemical measruing system having reduced peristaltic pump noise, said system including a high impedance measuring electrode for analyzing a fluid sample, a peristaltic pump having an elastomeric tubing streteched over rollers, and a fluid conduit extending from a first end of said elastomeric tubing to said measuring electrode, said rollers being movable over said elastomeric tubing for moving said fluid sample through said fluid conduit between said pump and said measuring electrode, said improvement comprising:
  a nonconductive fluid segment having a first impedance, said fluid segment being disposed in said fluid conduit for electrically isolating said pump and said measuring electrode; and
  an AC capacitive ground having a second impedance less than said first impedance, said AC capacitive ground being electrically connected to said fluid sample adjacent said first end of said peristaltic tubing for damping the peristaltic pump noise generated by said pump without significantly affecting the response time or precision of said measuring electrode.

2. The system of claim 1 wherein said first impendance is at least about double that of said second impedance.

3. The system of claim 2 wherein said fluid segment is a gas or liquid selected from the group consisting of air, nitrogen, carbon dioxide, argon, fluorocarbon liquid and liquid silicone.

4. The system of claim 3 wherein said fluid segment is greater than about 0.5 inches in length.

5. The system of claim 4 wherein said fluid segment is air and is greater than about two inches in length.

6. The system of claim 1 wherein the value of the capacitance of said AC capacitive ground is selected to damp said peristaltic pump noise by at least about 60% without significantly reducing the response time or precision of measurement of said measuring electrode.

7. The system of claim 6 wherein said measuring electrode has an impedance of from about 100 to about 3,000 megaohms and said AC capacitive ground has a capacitance of from about 0.1 to about 10 microfarads.

8. The system of claim 7 wherein said first impedance is at least about double that of said second impedance.

9. The system of claim 7 wherein said measuring electrode has an impedance of from about 500 to about 1,500 megaohms and said AC capacitive ground has a capacitance of from about 0.1 to about 1.0 microfarad.

10. The system of claim 9 wherein said first impedance is at least about double that of said second impedance.

11. The system of claim 10 wherein said elastomeric tubing is silicone impregnated with an electrically conductive material selected from the group consisting of metal and carbon.

12. The system of claim 10 wherein said fluid segment is air and is greater than about two inches in length.

13. The system of claim 1 wherein said AC capacitive ground includes a first electrically conductive tubular means disposed in fluid relationship between said first end of said elastomeric tubing and said fluid conduit for electrically connecting said AC capacitive ground to said fluid sample.

14. The system of claim 13 further including a second electrically conductive tubular means disposed in fluid relationship adjacent a second end of said elastomeric tubing for electrically connecting said AC capacitive ground to said fluid sample.

15. The system of claim 1 wherein said AC capacitive ground includes a first electrically conductive probe means in contact with said fluid sample adjacent said first end of said elastomeric tubing for electrically connecting said AC capacitive ground to said fluid sample.

16. The system of claim 15 wherein said AC capacitive ground includes a second electrically conductive probe means in contact with said fluid sample adjacent a second end of said elastomeric tubing for electrically connecting said AC capacitive ground to said fluid sample.

17. The system of claim 1 wherein said elastomeric tubing is conductive and said AC capacitive ground is electrically connected to said fluid sample via said elastomeric tubing.

18. A process for reducing peristaltic pump noise in a high impedance electrochemical measuring system which includes a high impedance measuring electrode for analyzing a fluid sample, a peristaltic pump having an elastomeric tubing stretched over rollers, and a fluid conduit extending from a first end of said elastomeric tubing to said measuring electrode, said rollers being movable over said elastomeric tubing for moving said fluid sample through said fluid conduit between said pump and said measuring electrode, said improvement comprising:

electrically isolating said pump and said measuring electrode by inserting a nonconductive fluid segment having a first impedance in said fluid conduit;

damping the peristaltic pump noise generated by said pump without significantly affecting the response time or precision of said measuring electrode by electrically connecting an AC capacitive ground having a second impedance less than said first impedance to said fluid sample adjacent said first end of said peristaltic tubing.

* * * * *